(12) United States Patent
Wang et al.

(10) Patent No.: US 12,090,055 B2
(45) Date of Patent: Sep. 17, 2024

(54) CLAMPING INSTRUMENT

(71) Applicants: SHANGHAI HUIHE HEALTHCARE TECHNOLOGY CO., LTD., Shanghai (CN); SHANGHAI HUIHE MEDICAL CO., LTD., Shanghai (CN)

(72) Inventors: Bao Wang, Shanghai (CN); Jun Xu, Shanghai (CN); Lin Lin, Shanghai (CN)

(73) Assignees: SHANGHAI HUIHE HEALTHCARE TECHNOLOGY CO., LTD., Shanghai (CN); SHANGHAI HUIHE MEDICAL CO., LTD., Shanghai (CN)

( * ) Notice: Subject to any disclaimer, the term of this patent is extended or adjusted under 35 U.S.C. 154(b) by 0 days.

(21) Appl. No.: 18/573,429

(22) PCT Filed: Aug. 2, 2022

(86) PCT No.: PCT/CN2022/109793
§ 371 (c)(1),
(2) Date: Dec. 21, 2023

(87) PCT Pub. No.: WO2023/029861
PCT Pub. Date: Mar. 9, 2023

(65) Prior Publication Data
US 2024/0261103 A1  Aug. 8, 2024

(30) Foreign Application Priority Data

Aug. 30, 2021 (CN) .......................... 202110999729.4

(51) Int. Cl.
*A61F 2/24* (2006.01)
(52) U.S. Cl.
CPC ............ *A61F 2/2466* (2013.01); *A61F 2/246* (2013.01); *A61F 2220/0016* (2013.01)

(58) Field of Classification Search
CPC . A61F 2/246; A61F 2/2466; A61F 2220/0016
See application file for complete search history.

(56) References Cited

U.S. PATENT DOCUMENTS

2013/0066342 A1  3/2013  Dell et al.
2024/0033084 A1*  2/2024  Lv .......................... A61F 2/246

FOREIGN PATENT DOCUMENTS

| CN | 110403670 A | 11/2019 |
| CN | 111772874 A | 10/2020 |

(Continued)

OTHER PUBLICATIONS

Chinese Patent Office, Office Action mailed Oct. 13, 2021, in Application No. 202110999729.4.

(Continued)

*Primary Examiner* — Brian A Dukert
*Assistant Examiner* — Rebecca Lynee Zimmerman
(74) *Attorney, Agent, or Firm* — Faegre Drinker Biddle & Reath LLP (57) ABSTRACT

A clamping instrument (10), mainly comprising: a clamping base (20), a driving base (30), a clamping structure (40), which forms different clamping angles according to the distance between the clamping base (20) and the driving base (30); and a fine adjustment member (50), wherein the fine adjustment member (50) and the driving base (30) can be separated from each other or connected to each other, such that the driving base (30) can move rapidly or step by step relative to the clamping base (20), thereby achieving the aim of rapidly adjusting or finely adjusting the clamping angle of the clamping structure.

11 Claims, 13 Drawing Sheets

(56) References Cited

FOREIGN PATENT DOCUMENTS

| | | |
|---|---|---|
| CN | 111772875 A | 10/2020 |
| CN | 111938870 A | 11/2020 |
| CN | 212490263 U | 2/2021 |
| CN | 112656546 A | 4/2021 |
| CN | 113017929 A | 6/2021 |
| CN | 113208777 A | 8/2021 |
| CN | 113208778 A | 8/2021 |
| CN | 113208779 A | 8/2021 |
| CN | 113425461 A | 9/2021 |
| WO | WO 2018-018873 A1 | 2/2018 |

OTHER PUBLICATIONS

Chinese Patent Office, Office Action mailed Nov. 2, 2021, in Application No. 202110999729.4.

* cited by examiner

CLAMPING INSTRUMENT

CROSS-REFERENCE TO RELATED APPLICATIONS

The present application is a national stage application of International Application No. PCT/CN2022/109793, filed Aug. 2, 2022, which claims priority to China Application No. 202110999729.4, filed Aug. 30, 2021, the disclosures of which are hereby incorporated by reference in their entireties.

TECHNICAL FIELD

The embodiments of the present application relate to the technical field of medical instruments, and in particular to a clamping instrument.

BACKGROUND

The mitral valve, tricuspid valve, aortic valve, and pulmonary valve commonly suffer from valvular insufficiency. Taking the mitral valve as an example, during the cardiac contraction phase, a portion of the blood from the left ventricle regurgitates through the incompetent mitral valve into the left atrium. The left atrium simultaneously receives blood from the regurgitation in the left ventricle and blood from the pulmonary veins. This leads to a significant increase in left atrial blood volume and elevated pressure, resulting in left atrial hypertrophy.

During the cardiac diastolic phase, a greater amount of blood flows from the left atrium into the left ventricle, leading to left ventricular hypertrophy due to intensified contraction. After progressing from compensated stage to decompensated stage, both the left atrium and left ventricle experience heart failure, subsequently leading to pulmonary congestion, pulmonary hypertension, right ventricular hypertrophy, right atrial enlargement, right heart failure, and systemic congestion.

Conventional treatment methods include aggressive surgical approaches or palliative use of drugs to counter inevitable heart failure. Surgical approaches further include valve replacement surgery and valvuloplasty. For surgical approaches, the typical open-chest surgery is highly invasive, requiring the establishment of extracorporeal circulation, and it carries a high incidence of complications and infection risk. This results in many patients being unable to tolerate the substantial surgical risks and being left with no choice but to reluctantly await death.

Currently, there are few domestically approved minimally invasive catheter-based products for treating mitral and tricuspid valve regurgitation. These products all require structural changes to the heart during treatment, imposing significant pressure and discomfort on the post-operative heart.

Therefore, there is an urgent need for a product that does not require altering the heart's structure, while still being able to treat valve regurgitation through a minimally invasive approach.

SUMMARY

Given the aforementioned issues, the present application provides a clamping instrument to overcome or at least partially address the aforementioned issues.

The embodiments of the present application provide a clamping instrument, comprising a clamping base; a driving base; a clamping structure connected respectively to the clamping base and the driving base, with different included angles formed based on different spacing distances between the clamping base and the driving base; and a fine adjustment member connected to the clamping base and connected to or disconnected from the driving base, wherein when the fine adjustment member is disconnected from the driving base, the driving base can be moved rapidly relative to the clamping base to rapidly adjust the included angle; when the fine adjustment member is connected to the driving base, the driving base can be moved step by step relative to the clamping base to finely adjust the included angle.

Optionally, the clamping instrument further comprises a quick adjustment member, which passes axially through the driving base and is connected to the fine adjustment member, enabling the driving base to be coaxially connected to the clamping base, wherein when the fine adjustment member is connected to the quick adjustment member, and the fine adjustment member is disconnected from the driving base, the driving base can be moved rapidly along an axial direction of the quick adjustment member relative to the clamping base to rapidly adjust the included angle.

Optionally, the fine adjustment member further comprises a driving positioning part, and the driving base comprises a driving passage part, wherein side walls of the driving positioning part and the driving passage part respectively comprise threads; the fine adjustment member can be driven by the quick adjustment member to rotate circumferentially relative to the driving base, enabling the driving positioning part to be threadedly connected to or disconnected from the driving base; in a state where the driving positioning part is threadedly connected to the driving base, the fine adjustment member can be driven by the quick adjustment member to rotate circumferentially relative to the driving base, enabling the driving positioning part to move step by step along an axial direction of the driving base, thus finely adjusting the included angle.

Optionally, the driving base further comprises a guiding part adjacent to the driving passage part, which is configured to guide engagement between the driving positioning part and the driving passage part.

Optionally, the fine adjustment member further comprises a clamping positioning part, and the clamping base further comprises a clamping passage part, wherein the clamping positioning part is disposed in the clamping passage part, and is positioned axially and rotated circumferentially relative to the clamping passage part.

Optionally, the clamping instrument further comprises a first engaging part disposed circumferentially around the clamping positioning part and a second engaging part disposed circumferentially around the clamping passage part, enabling the clamping positioning part to be movably engaged in the clamping passage part, wherein one of the first engaging part and the second engaging part comprises a circular groove, and the other of the first engaging part and the second engaging part comprises an engaging rib or an engaging ring.

Optionally, the quick adjustment member can be disconnected from the fine adjustment member to be removed from the clamping instrument.

Optionally, the clamping structure comprises at least two clamping arms, and each of the clamping arms is pivotally connected to the clamping base and can pivot relative to the clamping base under the action of movement of the clamping base relative to the driving base, thereby forming the different included angles, wherein the included angle formed by each of the clamping arms may not be less than a tissue surface curvature of a target tissue, so as to fully expose respective root portion of each of the clamping arms and/or a surface of the clamping base adjacent to the target tissue.

Optionally, the included angle formed by each of the clamping arms ranges from 0 degrees to 360 degrees.

Optionally, the clamping arm comprises a clamping groove with an arc-shaped cross-section, and the clamping instrument further comprises spikes extending from a groove bottom of the clamping groove toward a groove opening of the clamping groove.

Optionally, the clamping structure further comprises at least two driving arms, and each of the driving arms is connected to the driving base and each of the clamping arms, wherein when the clamping base moves relative to the driving base, each of the clamping arms can be driven by each of the driving arms to pivot relative to the clamping base.

Optionally, the clamping instrument further comprises an anchoring member, which can be rotated circumferentially relative to the clamping base to anchor the target tissue.

Optionally, the anchoring member can be moved axially relative to the clamping base to switch between a clamping position and a non-clamping position, wherein when the anchoring member is in the non-clamping position, the anchoring member can anchor the target tissue; when the anchoring member is in the clamping position, the clamping structure can clamp the target tissue anchored to the anchoring member.

In summary, the clamping instrument provided by the embodiments of the present application, through the combined design of the fine adjustment member and the driving base, enables rapid and fine adjustment of the included angle, thereby enhancing the operational convenience of the instrument.

Moreover, the clamping structure of the present application can provide an included angle ranging from 0 to 360 degrees, such that during the clamping process, the target tissue to be clamped can come into full contact with the exposed root portion of each of the clamping arms and/or the surface of the clamping base adjacent to the target tissue, thereby increasing the contact area between the target tissue and the clamping structure and thus enhancing the clamping stability.

In addition, by designing a spike-like structure extending from the groove bottom to the groove opening of the clamping groove on the clamping arm, the depth of the spike penetrating into the target tissue can be increased in a clamping state, such that a better anti-detachment effect is achieved, and the connection stability between the target tissue and the clamping structure is further enhanced.

BRIEF DESCRIPTION OF THE DRAWINGS

In order to more clearly illustrate the embodiments of the present application or the technical solutions in the prior art, the drawings used in the embodiments or description of the prior art will be briefly described below. It is obvious that the drawings in the following description are only some embodiments in the embodiments of the present application, and based on these drawings, other drawings can be obtained by those skilled in the art.

FIGS. 3 to 6 are schematic diagrams of the clamping instrument in different operational states according to the present application, wherein FIGS. 4 and 6 are side-sectional views of FIGS. 3 and 5, respectively.

REFERENCE NUMERALS FOR MEMBERS

10: a clamping instrument;
20: a clamping base;
22: a clamping passage part;
24: surface (clamping base);
30: a driving base;
32: a driving passage part;
34: a guiding part;
40: a clamping structure;
42: a clamping arm;
422: a root portion;
44: a clamping groove;
46: a driving arm;
462, 464: pivoting shafts;
48: a spike;
50: a fine adjustment member;
52: a driving positioning part;
54: a clamping positioning part;
60: a delivery system;
62: a quick adjustment member;
64: a positioning member;
72: a first engaging part;
74: a second engaging part;
76: a circular groove;
78: an engaging ring;
80: an anchoring member.

DETAILED DESCRIPTION

To facilitate a better understanding of the technical solutions in the embodiments of the present application, the following description will be provided, with reference to the accompanying drawings, to present a clear and comprehensive account of the technical solutions in the embodiments of the present application. It is evident that the described embodiments are only a portion of the embodiments of the present application, rather than the entirety. Based on the embodiments in the embodiments of the present application, all other embodiments that those skilled in the art derive should fall within the scope of protection of the present application.

The following will further illustrate the specific implementation of the embodiments of the present application with reference to the accompanying drawings.

The clamping instrument 10 of the embodiment can serve as an implant for ring annuloplasty in the field of structural heart disease intervention therapy. It can be delivered through minimally invasive routes such as vascular access or through atrial appendage to reach specified anatomical locations, enabling the repair treatment of cardiac valve annuli (e.g., mitral valve, tricuspid valve, aortic valve, pulmonary valve, etc.).

As shown in FIGS. 1 to 7, the clamping instrument 10 of the present application mainly comprises a clamping base 20, a driving base 30, a clamping structure 40, and a fine adjustment member 50.

In this embodiment, the clamping structure 40 is connected respectively to the clamping base 20 and the driving base 30, and different included angles can be formed based on the different spacing distances between the clamping base 20 and the driving base 30.

In this embodiment, the clamping structure 40 may comprise at least two clamping arms 42 and at least two driving arms 46. The positions of the respective clamping arms 42 correspond to the positions of the respective driving arms 46. Each clamping arm 42 is pivotally connected to the clamping base 20, and each driving arm 46 is connected to the driving base 30 and each clamping arm 42. For example, the relative ends of the driving arm 46 can be pivotally connected to the driving base 30 and the clamping arm 42 via pivoting shafts 462 and 464, respectively (see FIG. 7).

In this embodiment, when the clamping base 20 moves relative to the driving base 30, each clamping arm 42 can be driven by each driving arm 46 to pivot relative to the clamping base 20, thereby forming different included angles.

Figure 1:
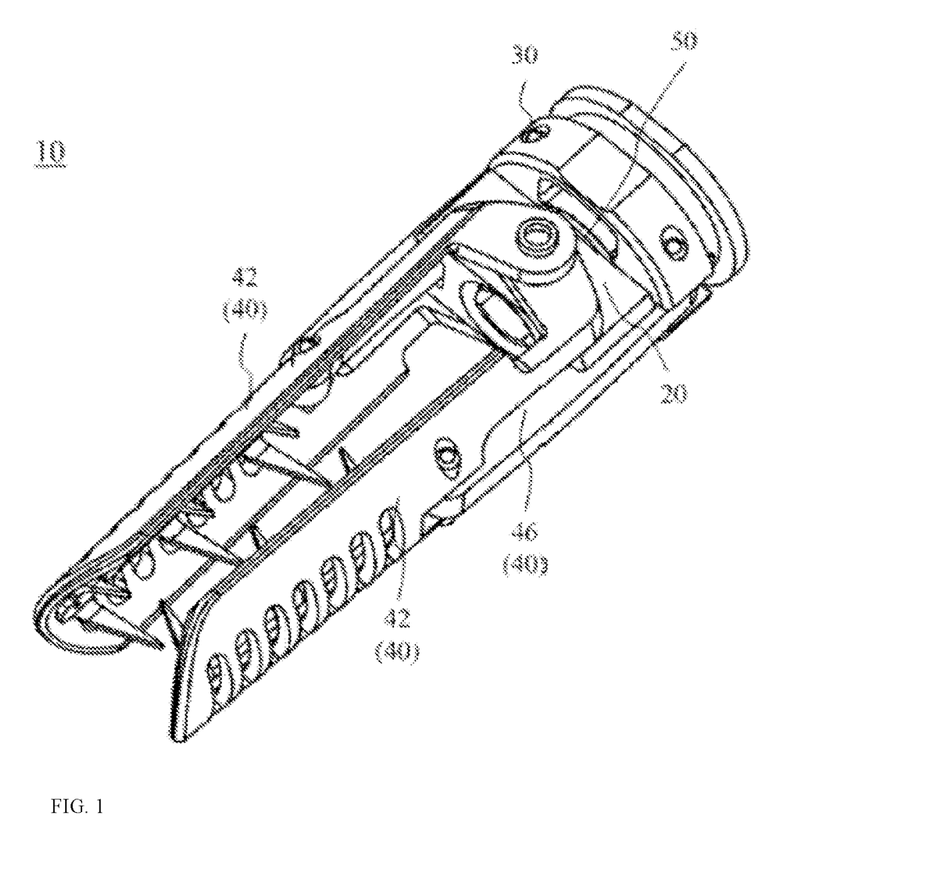
FIGS. 1 and 2 show the schematic diagrams of the overall structure of the clamping instrument in different operational states according to the present application.
Figure 2:
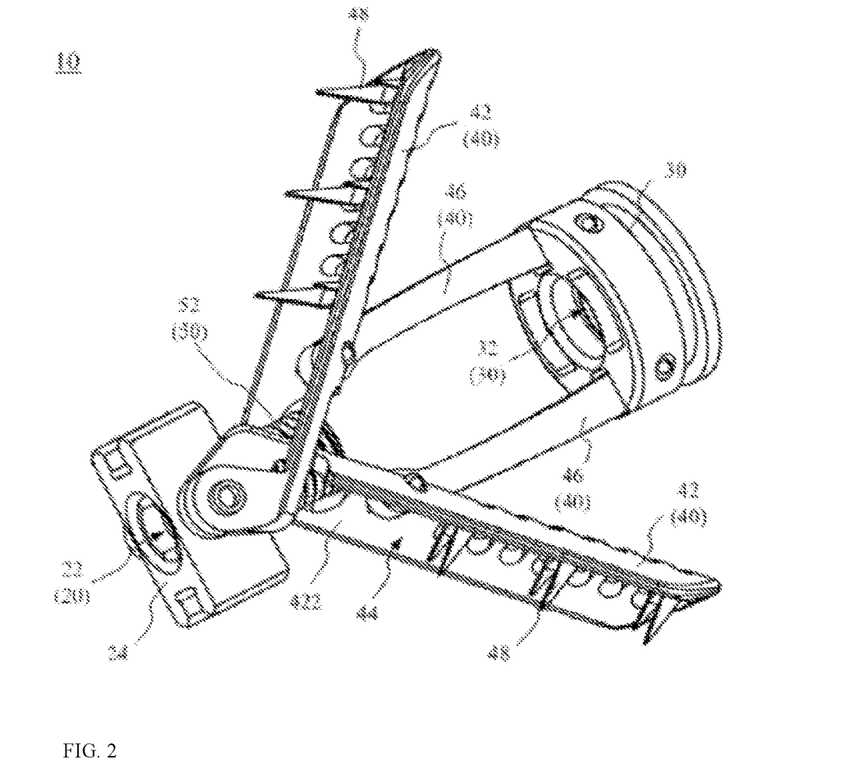
Figure 3:
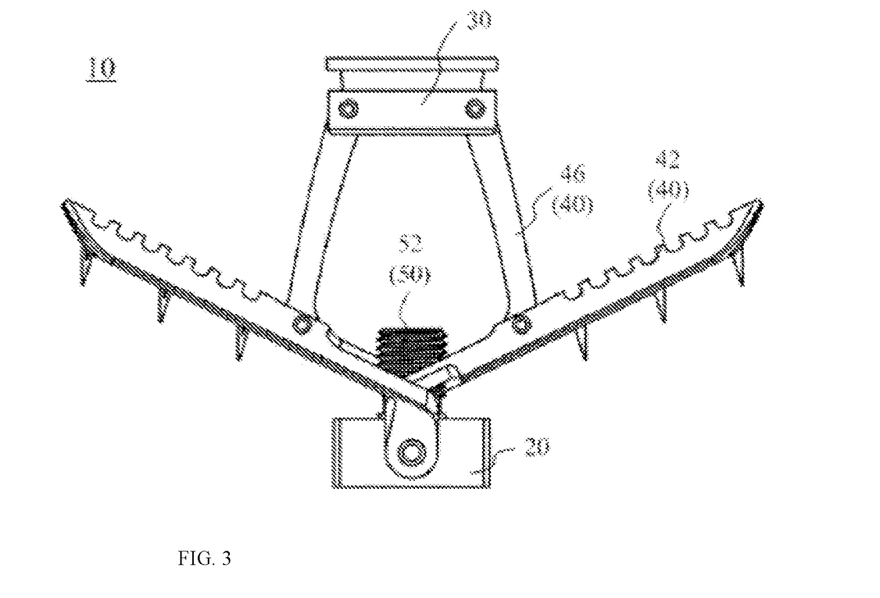
Figure 4:
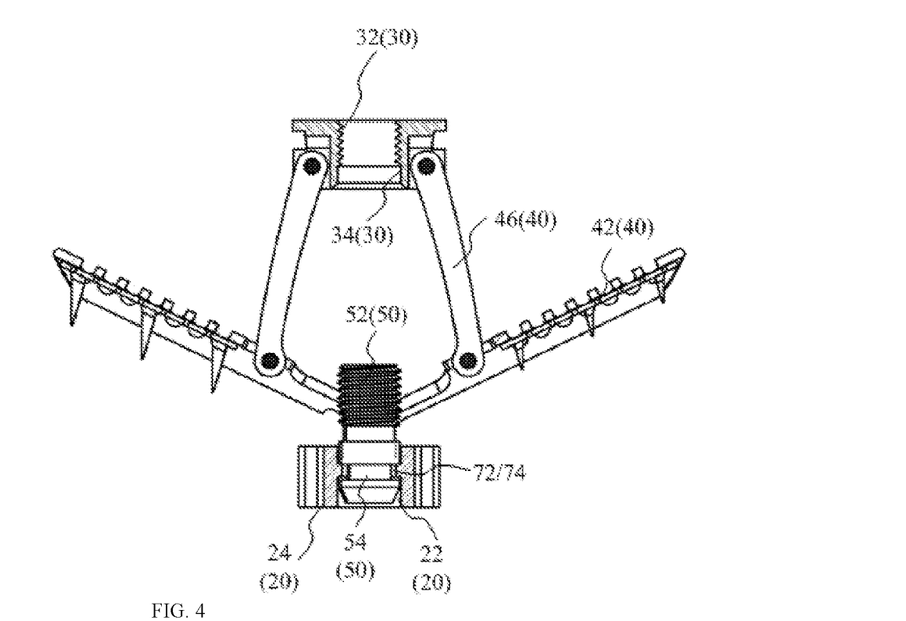

Optionally, the included angle formed by each of the clamping arms 42 may not be less than the tissue surface curvature of the target tissue, so as to fully expose the root portion 422 of each of the clamping arms 42 and/or the surface 24 of the clamping base 20 adjacent to the target tissue (see FIGS. 2 to 4). By this design, the target tissue to be clamped can come into full contact (abutment) with the exposed root portion 422 of each clamping arm 42 and/or the surface 24 of the clamping base 20 adjacent to the target tissue, thereby increasing the contact area between the target tissue and each clamping arm 42 and thus enhancing the clamping stability of the clamping structure 40.

In this embodiment, the included angle formed by each of the clamping arms 42 may range from 0 degrees to 360 degrees.

Preferably, each clamping arm 42 may comprise a clamping groove 44 with an arc-shaped cross-section, and the clamping instrument 10 further comprises spikes 48 extending from the groove bottom of the clamping groove 44 toward the groove opening of the clamping groove 44. By this design, the depth at which the spikes 48 penetrate into the target tissue in the clamped state is effectively increased, thereby providing enhanced anti-detachment effects and further enhancing the connection stability between the target tissue and the clamping structure 40 (clamping arms 42).

Optionally, the fine adjustment member 50 can be connected to the clamping base 20 and can be connected to or disconnected from the driving base 30.

In one embodiment, when the fine adjustment member 50 is disconnected from the driving base 30, the driving base 30 can be moved rapidly relative to the clamping base 20 to rapidly adjust the included angle of the clamping structure 40 (see the states shown in FIGS. 2 to 4).

Figure 5:
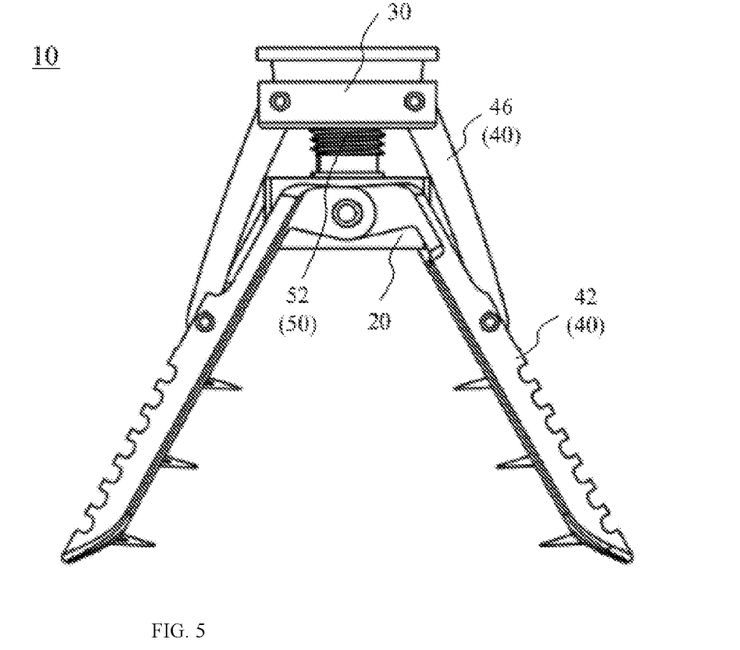
Figure 6:
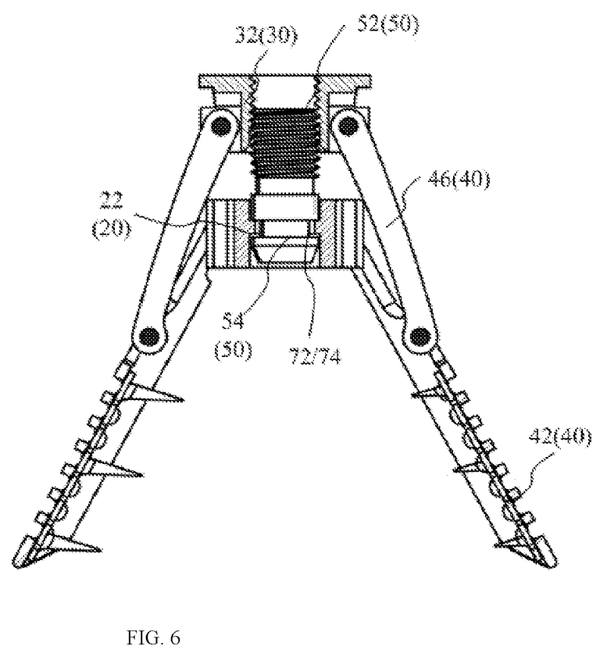

In another embodiment, when the fine adjustment member 50 is connected to the driving base 30, the driving base 30 can be moved step by step relative to the clamping base 20 to finely adjust the included angle of the clamping structure 40 (see the states shown in FIGS. 5 and 6).

Specifically, the fine adjustment member 50 can be rotated circumferentially and positioned axially relative to the clamping base 20, and it can be rotated circumferentially and moved axially relative to the driving base 30. Thus by causing the fine adjustment member 50 to rotate circumferentially, the spacing distance between the clamping base 20 and the driving base 30 can be finely adjusted.

Optionally, the clamping instrument 10 further comprises a quick adjustment member 62. Referring to FIGS. 8 to 11, the quick adjustment member 62 can pass axially through the driving base 30 and be connected to the fine adjustment member 50, enabling the driving base 30 to be coaxially connected to the clamping base 20.

Figure 8:
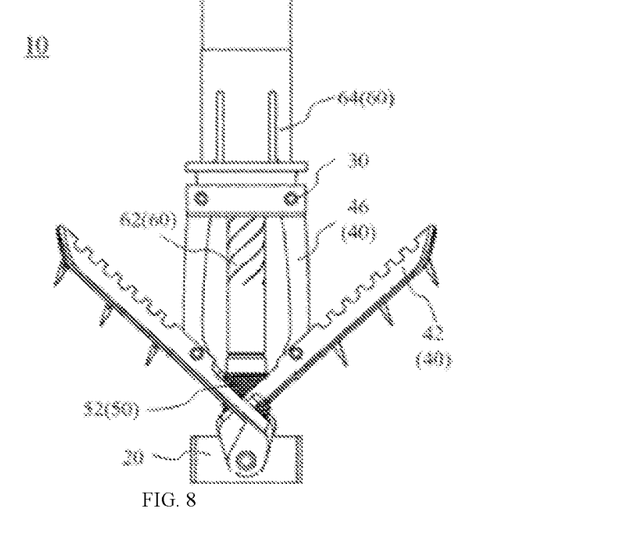
FIGS. 8 to 11 are structural schematic diagrams of the quick adjustment member of the clamping instrument according to the present application.
Figure 9:
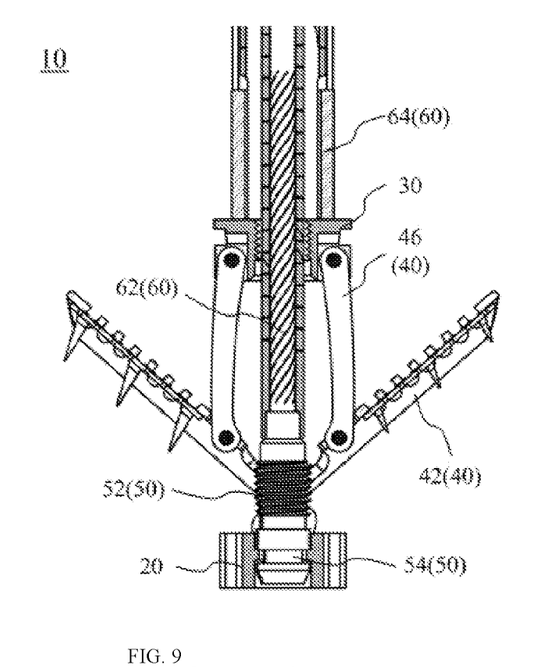
Figure 10:
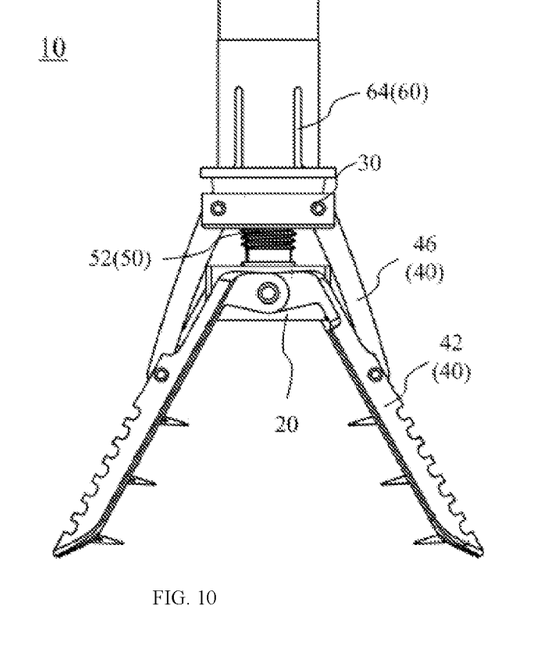

Specifically, when the fine adjustment member 50 is connected to the quick adjustment member 62, and meanwhile the fine adjustment member 50 is disconnected from the driving base 30, the driving base 30 can be rapidly moved along the axial direction of the quick adjustment member 62 relative to the clamping base 20, allowing for quick adjustment of the included angle of the clamping structure 40 (see the states shown in FIGS. 8 and 9).

Figure 7:
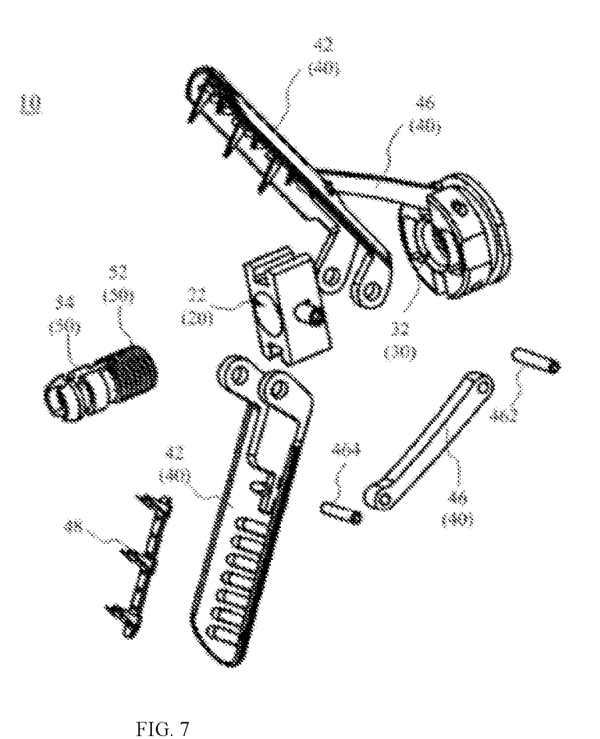
FIG. 7 is a schematic diagram of the exploded structure of the clamping instrument according to the present application.

Optionally, the fine adjustment member 50 may comprise a driving positioning part 52, and the driving base 30 may comprise a driving passage part 32 (see FIGS. 2 and 7).

The side walls of the driving positioning part 52 and the driving passage part 32 respectively comprise threads, enabling the fine adjustment member 50 to be threadedly connected to the driving base 30.

In one embodiment, the fine adjustment member 50 can be driven by the quick adjustment member 62 to rotate circumferentially (e.g., clockwise) relative to the driving base 30, enabling the driving positioning part 52 to be threadedly connected to the driving passage part 32 of the driving base 30. Alternatively, the fine adjustment member 50 can be driven to rotate circumferentially in the reverse direction (e.g., counterclockwise) relative to the driving base 30 via the quick adjustment member 62, enabling the driving positioning part 52 to disconnect from the driving passage part 32.

In one embodiment, in the state where the driving positioning part 52 is threadedly connected to the driving passage part 32, the fine adjustment member 50 can be driven by the quick adjustment member 62 to rotate circumferentially relative to the driving passage part 32, enabling the driving positioning part 52 (fine adjustment member 50) to move step by step along the axial direction of the driving base 30, thus finely adjusting the included angle of the clamping structure 40.

In this embodiment, the quick adjustment member 62 can also be disconnected from the fine adjustment member 50 to be removed from the clamping instrument 10.

For example, the quick adjustment member 62 can serve as a component of a delivery system 60 (see FIGS. 8 to 11), and after completing the clamping operation on the target tissue, the quick adjustment member 62 is disconnected from the fine adjustment member 50 to be removed from the clamping instrument 10. This reduces the volume of the clamping instrument left in the patient's body, effectively lowering the risk of postoperative infection.

Specifically, the delivery system 60 can further comprise a positioning member 64. In this embodiment, both the positioning member 64 and the quick adjustment member 62 may form a mutually nested inner and outer sleeve structure.

The positioning member 64 can be connected to the driving base 30, and the quick adjustment member 62 can be connected to the fine adjustment member 50. The spacing distance between the clamping base 20 and the driving base 30 is adjusted rapidly or finely by axially moving or circumferentially rotating the quick adjustment member 62 relative to the positioning member 64.

Preferably, the driving base 30 further comprises a guiding part 34 adjacent to the driving passage part 32 (see FIG. 4), which is configured to guide the engagement between the driving positioning part 52 and the driving passage part 32.

As shown in the figure, in this embodiment, the guiding part 34 at the front end of the driving passage part 32 can be designed as a passage opening with smooth side walls, facilitating the smooth engagement of the driving positioning part 52 of the fine adjustment member 50 with the driving passage part 32 via the guiding part 34.

Optionally, the fine adjustment member 50 may further comprise a clamping positioning part 54, and the clamping base 20 may further comprise a clamping passage part 22 (see FIGS. 2 and 7). The clamping positioning part 54 may be disposed in the clamping passage part 22, and be positioned axially and rotated circumferentially relative to the clamping passage part 22.

Specifically, the clamping instrument 10 further comprises a first engaging part 72 disposed circumferentially around the clamping positioning part 54 and a second engaging part 74 disposed circumferentially around the clamping passage part 22, enabling the clamping positioning part 54 to be movably engaged in the clamping passage part 22 (see FIGS. 4 and 6).

In this embodiment, the first engaging part 72 may comprise a circular groove, and the second engaging part 74 may comprise an engaging rib or an engaging ring (as the example shown in FIGS. 4 and 6). However, this is not limited, and it may also be designed that the first engaging part 72 comprises an engaging rib or an engaging ring, and the second engaging part 74 comprises a circular groove. This is not limited by the present application.

Referring to FIGS. 12 to 15, optionally, the clamping instrument 10 may further comprise an anchoring member 80, which can be rotated circumferentially relative to the clamping base 20 to anchor the target tissue.

Optionally, the anchoring member 80 can be moved axially relative to the clamping base 20 to switch between a clamping position and a non-clamping position. When the anchoring member 80 is in the non-clamping position, the anchoring member can anchor the target tissue (see the states shown in FIGS. 12 and 13); when the anchoring member 80 is in the clamping position, the clamping structure 40 can clamp the target tissue anchored to the anchoring member 80 (see the states shown in FIGS. 14 and 15).

The following provides an illustrative description, with reference to FIGS. 16 to 19, of the method of using the clamping instrument 10 of the present application for performing heart valve annulus repair treatment.

Figure 11:
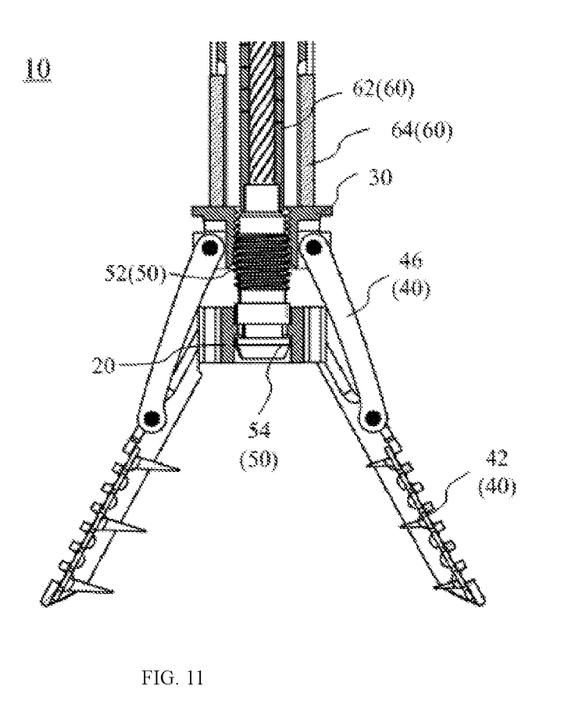
Figure 12:
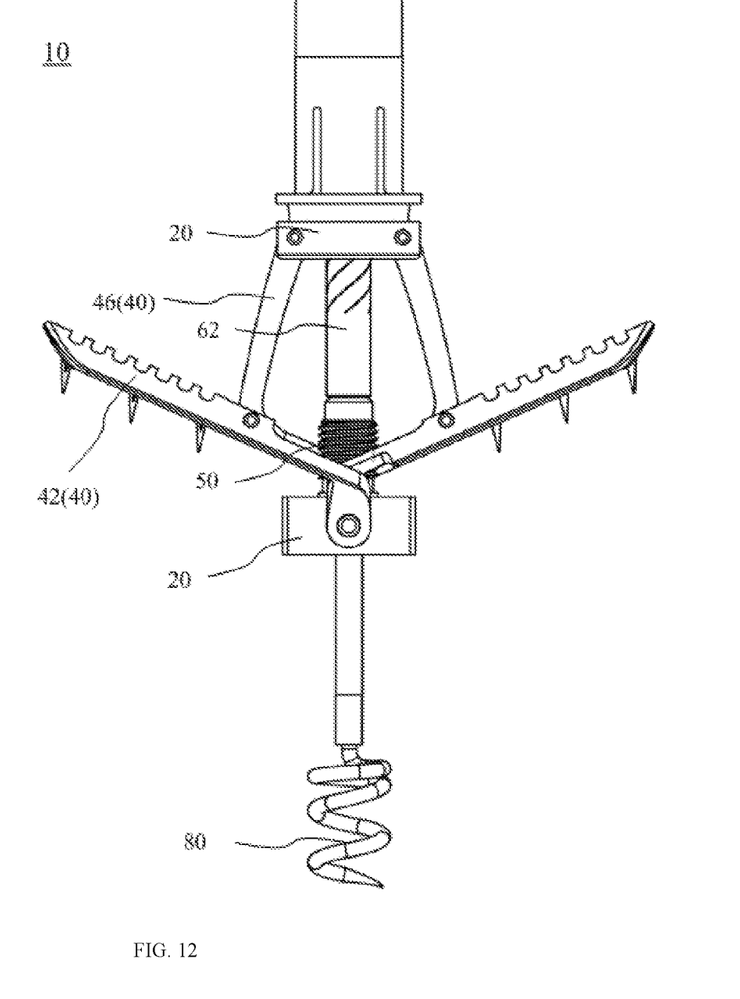
FIGS. 12 to 15 are exemplary schematic diagrams of the anchoring member of the clamping instrument according to the present application.
Figure 13:
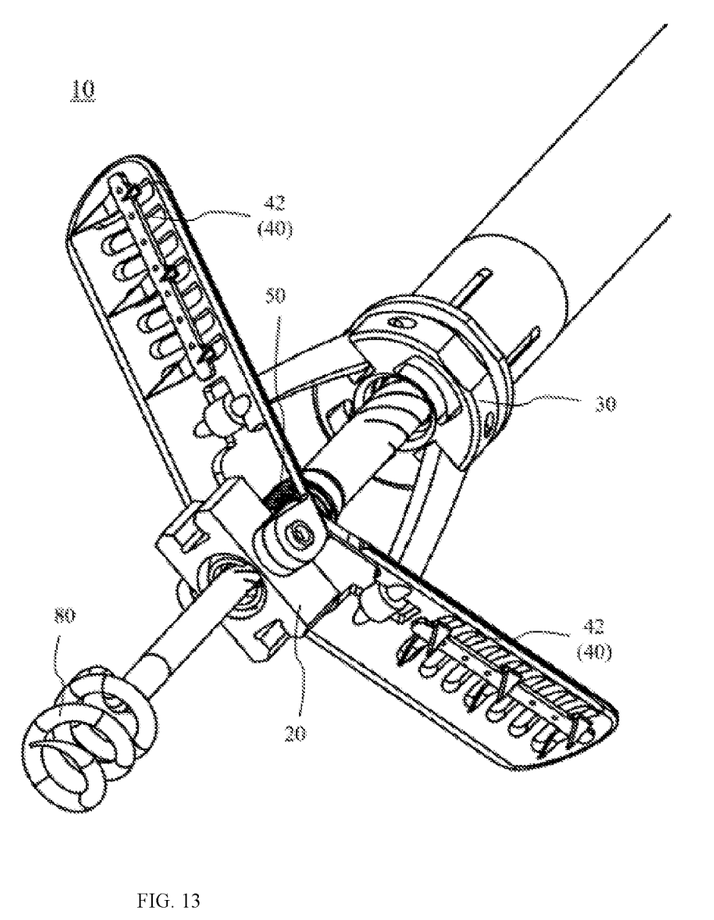
Figure 14:
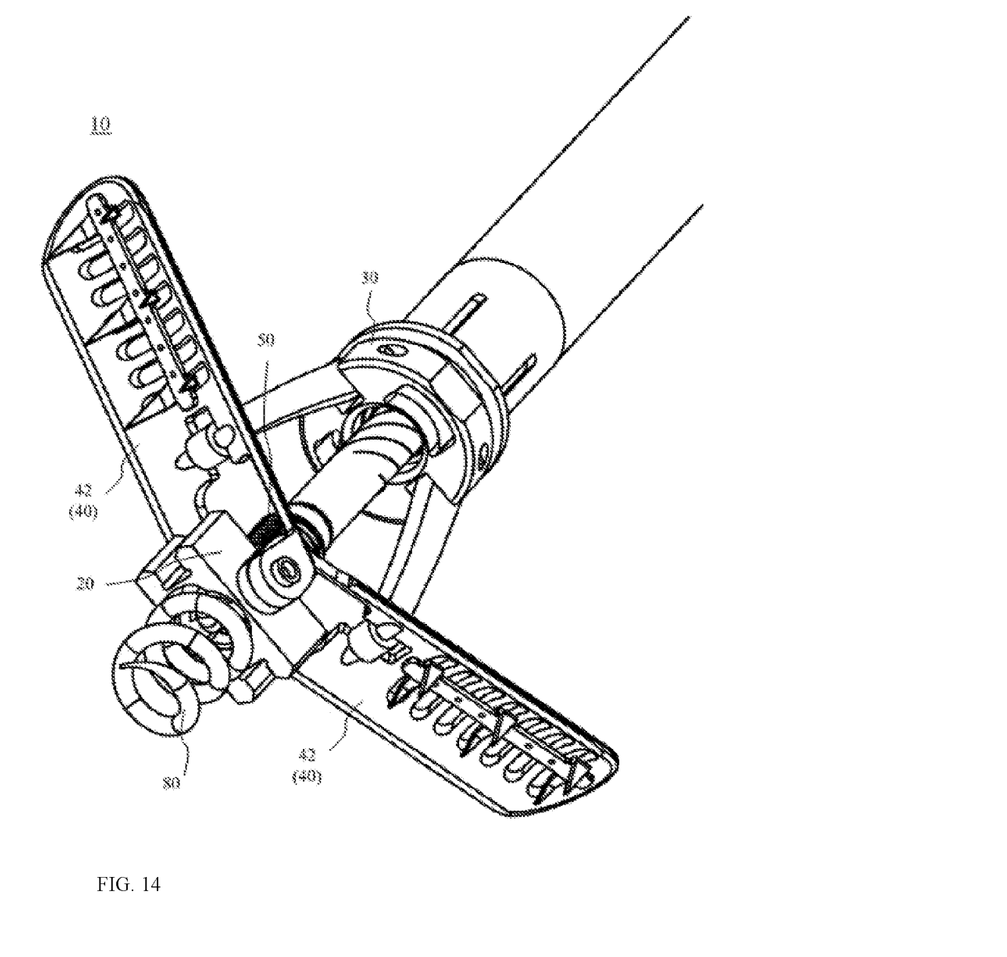
Figure 15:
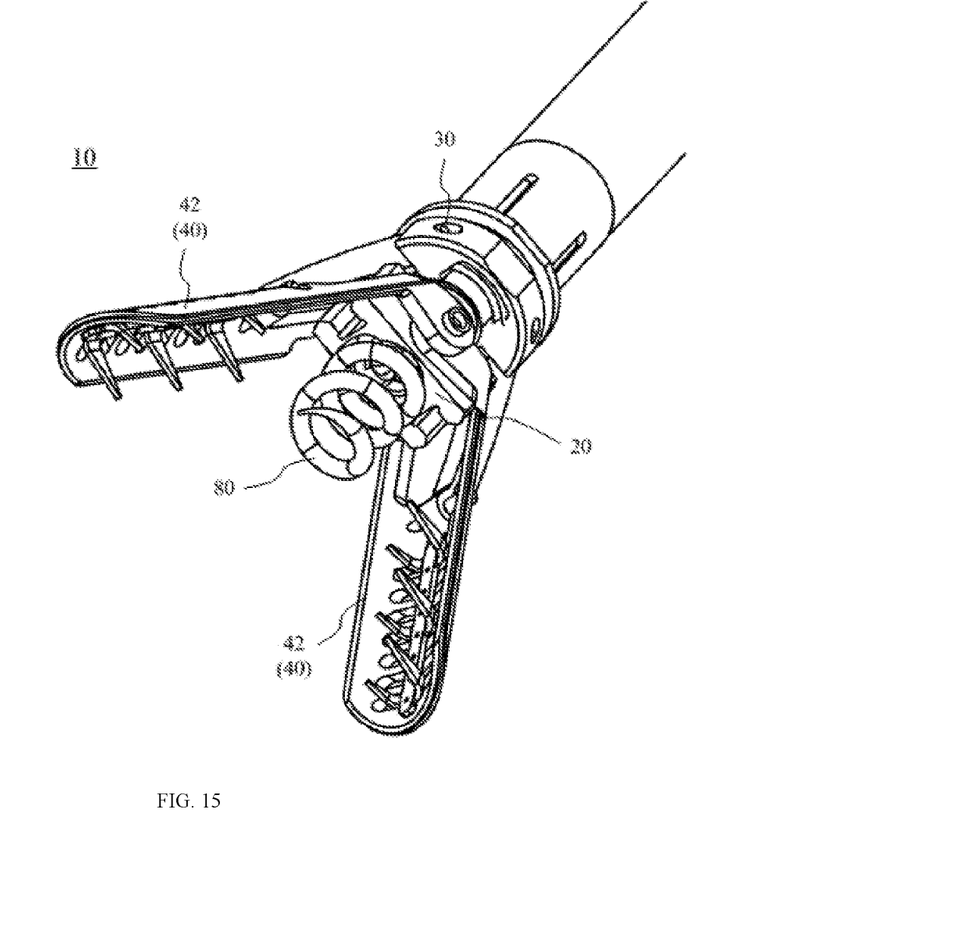
Figure 16:
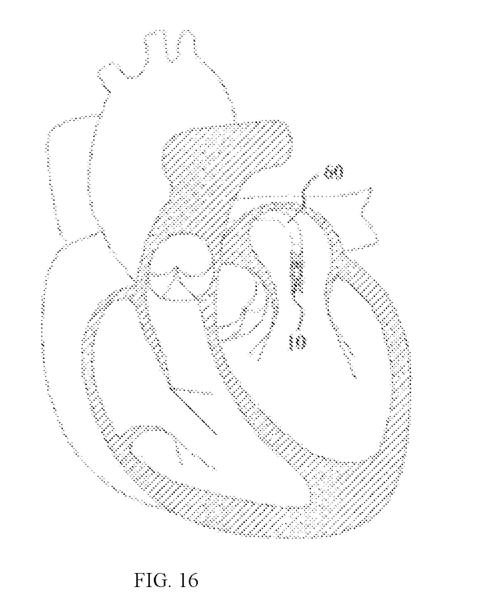
FIGS. 16 to 19 are exemplary schematic diagrams of the utilization of the clamping instrument according to the present application to clamp target tissues.

The quick adjustment member 62 and the positioning member 64 of the delivery system 60 are connected respectively to the driving base 30 and the fine adjustment member 50 of the clamping instrument 10 (see the states shown in FIGS. 9 and 11). The delivery system 60 is used to deliver the clamping instrument 10 to the vicinity of the target tissue to be repaired (such as the heart valve annulus) (see FIG. 16).

Figure 17:
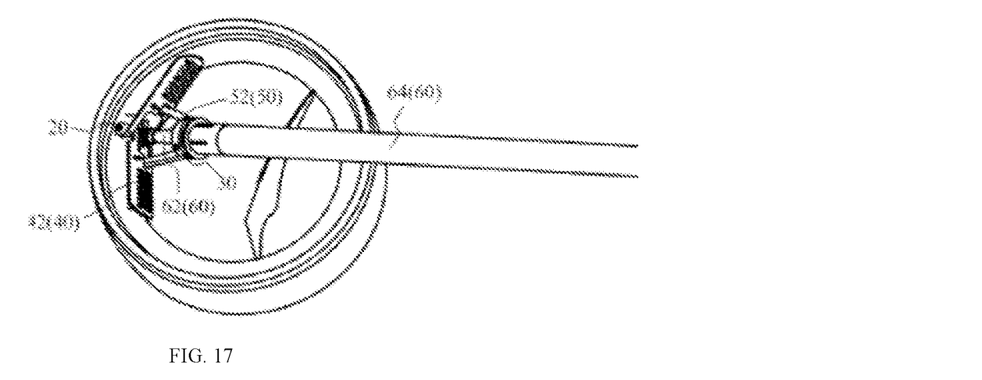
Figure 18:
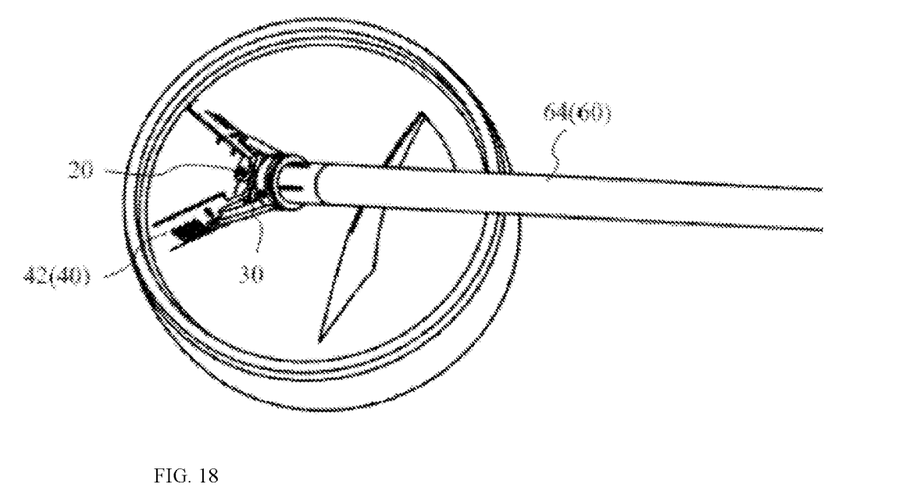

Referring to FIG. 17, by axially moving the quick adjustment member 62 relative to the positioning member 64, the clamping base 20 is driven to move rapidly toward the direction away from the driving base 30. This rapidly opens the two clamping arms 42 of the clamping structure 40, ensuring that the included angle formed by the two clamping arms 42 is not less than the tissue surface curvature of the target tissue. This exposes the respective root portion 422 of each of the clamping arms 42 and/or the surface 24 of the clamping base 20 adjacent to the target tissue, enabling the target tissue to be clamped to come into full abutment with the respective root portions 422 of the clamping arms 42 and/or the surface 24 of the clamping base 20 adjacent to the target tissue (see FIGS. 2 to 4).

By axially moving the quick adjustment member 62 in the reverse direction relative to the positioning member 64, the clamping base 20 is driven to move rapidly toward the direction close to the driving base 30. This rapidly closes the two clamping arms 42 of the clamping structure 40, that is, rapidly reduces the included angle of the clamping structure 40, until the fine adjustment member 50 abuts against the driving base 30 (see FIG. 18).

By circumferentially rotating the quick adjustment member 62 relative to the positioning member 64, the fine adjustment member 50 is threadedly connected to the driving base 30. In the state where the fine adjustment member 50 is threadedly connected to the driving base 30, by further controlling the fine adjustment member 50 to circumferentially rotate relative to the driving base 30, the driving base 30 is driven to move along the axis of the fine adjustment member 50 step by step, thereby finely adjusting the spacing distance between the driving base 30 and the clamping base 20, that is, finely adjusting the included angle of the clamping structure 40, until the clamping operation on the target tissue is completed.

Figure 19:
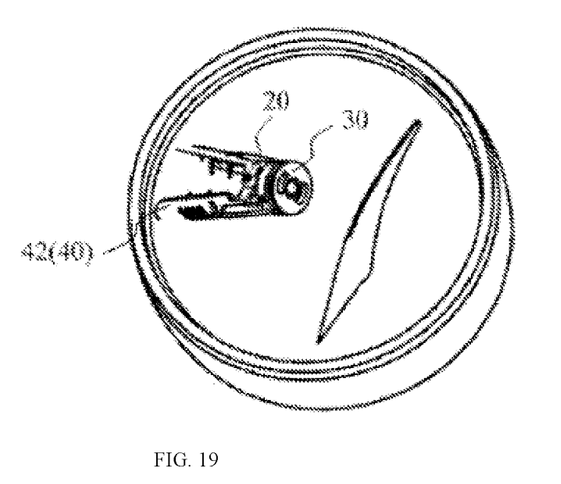

The quick adjustment member 62 and the positioning member 64 of the delivery system 60 are disconnected respectively from the fine adjustment member 50 and the driving base 30, and the delivery system 60 is removed, leaving only the clamping instrument 10 inside the patient's body and thus completing the clamping operation on the target tissue (such as the heart valve annulus) (see the states shown in FIG. 19). In summary, the clamping instrument provided by the present application allows for segmented adjustment of the included angle of the clamping structure with quick adjustment and fine adjustment methods, thereby enhancing the operational convenience of the clamping instrument.

Moreover, the present application achieves an included angle formed by the clamping structure that is not less than the tissue surface curvature of the target tissue. This enables the target tissue to be clamped to come into full contact with the root portions of the clamping arms and/or the clamping base, thereby increasing the contact area between the target tissue and the clamping structure and thus enhancing the clamping stability of the clamping structure.

In addition, the present application achieves an increased depth of spikes penetrating into the target tissue by extending the spikes from the groove bottom to the groove opening of the clamping groove, thereby enhancing the anti-detachment effects in the clamping state and further enhancing the connection stability between the clamping structure and the target tissue.

Finally, it should be noted that the above embodiments are only intended to illustrate the technical solutions in the embodiments of the present application, and should not limit the same; although the present application is described in detail with reference to the embodiments described above, it will be understood by those skilled in the art that, the technical solutions in the embodiments described above can still be modified, or some of the technical features can be equivalently replaced; and these modifications or replacements do not make the essence of the technical solutions depart from the spirit and scope of the technical solutions in the various embodiments of the present application.

The invention claimed is:

1. A clamping instrument, wherein the clamping instrument comprises:
a clamping base;
a driving base;
a clamping structure connected respectively to the clamping base and the driving base, with different included angles formed based on different spacing distances between the clamping base and the driving base; and
a fine adjustment member connected to the clamping base and connected to or disconnected from the driving base, wherein
when the fine adjustment member is disconnected from the driving base, the driving base can be moved rapidly relative to the clamping base to rapidly adjust the included angle;
when the fine adjustment member is connected to the driving base, the driving base can be moved step by step relative to the clamping base to finely adjust the included angle;
the clamping instrument further comprises a quick adjustment member, which passes axially through the driving base and is connected to the fine adjustment member, enabling the driving base to be coaxially connected to the clamping base,
wherein when the fine adjustment member is connected to the quick adjustment member, and the fine adjustment member is disconnected from the driving base, the driving base can be moved rapidly along an axial direction of the quick adjustment member relative to the clamping base to rapidly adjust the included angle;
the fine adjustment member further comprises a driving positioning part, and the driving base comprises a driving passage part,
wherein side walls of the driving positioning part and the driving passage part respectively comprise threads;
the fine adjustment member can be driven by the quick adjustment member to rotate circumferentially relative to the driving base, enabling the driving positioning part to be threadedly connected to or disconnected from the driving base;
in a state where the driving positioning part is threadedly connected to the driving base, the fine adjustment member can be driven by the quick adjustment member to rotate circumferentially relative to the driving base, enabling the driving positioning part to move step by step along an axial direction of the driving base, thus finely adjusting the included angle.

2. The clamping instrument according to claim 1, wherein the driving base further comprises a guiding part adjacent to the driving passage part, which is configured to guide engagement between the driving positioning part and the driving passage part.

3. The clamping instrument according to claim 1, wherein the fine adjustment member further comprises a clamping positioning part, and the clamping base further comprises a clamping passage part,
wherein the clamping positioning part is disposed in the clamping passage part, and is positioned axially and rotated circumferentially relative to the clamping passage part.

4. The clamping instrument according to claim 3, wherein the clamping instrument further comprises a first engaging part disposed circumferentially around the clamping positioning part and a second engaging part disposed circumferentially around the clamping passage part, enabling the clamping positioning part to be movably engaged in the clamping passage part,
wherein one of the first engaging part and the second engaging part comprises a circular groove, and the other of the first engaging part and the second engaging part comprises an engaging rib or an engaging ring.

5. The clamping instrument according to claim 3, wherein the quick adjustment member can be disconnected from the fine adjustment member to be removed from the clamping instrument.

6. The clamping instrument according to claim 1, wherein the clamping structure comprises at least two clamping arms, and each of the clamping arms is pivotally connected to the clamping base and can pivot relative to the clamping base under the action of movement of the clamping base relative to the driving base, thereby forming the different included angles,
wherein the included angle formed by each of the clamping arms may not be less than a tissue surface curvature of a target tissue, so as to fully expose respective root portion of each of the clamping arms and/or a surface of the clamping base adjacent to the target tissue.

7. The clamping instrument according to claim 6, wherein the included angle formed by each of the clamping arms ranges from 0 degrees to 360 degrees.

8. The clamping instrument according to claim 6, wherein the clamping arm comprises a clamping groove with an arc-shaped cross-section, and the clamping instrument further comprises spikes extending from a groove bottom of the clamping groove toward a groove opening of the clamping groove.

9. The clamping instrument according to claim 6, wherein the clamping structure further comprises at least two driving arms, and each of the driving arms is connected to the driving base and each of the clamping arms,
wherein when the clamping base moves relative to the driving base, each of the clamping arms can be driven by each of the driving arms to pivot relative to the clamping base.

10. The clamping instrument according to claim 6, wherein the clamping instrument further comprises an anchoring member, which can be rotated circumferentially relative to the clamping base to anchor the target tissue.

11. The clamping instrument according to claim 10, wherein the anchoring member can be moved axially relative to the clamping base to switch between a clamping position and a non-clamping position,
wherein when the anchoring member is in the non-clamping position, the anchoring member can anchor the target tissue; when the anchoring member is in the clamping position, the clamping structure can clamp the target tissue anchored to the anchoring member.

* * * * *